United States Patent
Majewski et al.

(10) Patent No.: US 7,884,331 B2
(45) Date of Patent: Feb. 8, 2011

(54) COMPACT AND MOBILE HIGH RESOLUTION PET BRAIN IMAGER

(75) Inventors: Stanislaw Majewski, Yorktown, VA (US); James Proffitt, Newport News, VA (US)

(73) Assignee: Jefferson Science Associates LLC, Newport News, VA (US)

(*) Notice: Subject to any disclaimer, the term of this patent is extended or adjusted under 35 U.S.C. 154(b) by 54 days.

(21) Appl. No.: 12/284,285

(22) Filed: Sep. 19, 2008

(65) Prior Publication Data
US 2010/0288935 A1 Nov. 18, 2010

(51) Int. Cl.
  *G01T 1/161* (2006.01)
(52) U.S. Cl. .................................................. 250/363.04
(58) Field of Classification Search ............ 250/363.03, 250/363.02, 363.04
See application file for complete search history.

(56) References Cited

U.S. PATENT DOCUMENTS

| | | | |
|---|---|---|---|
| 4,980,552 A | | 12/1990 | Cho et al. |
| 6,697,660 B1 | | 2/2004 | Robinson |
| 2004/0008810 A1 | * | 1/2004 | Nelson et al. .................. 378/19 |
| 2005/0082486 A1 | * | 4/2005 | Schlyer et al. ......... 250/363.01 |
| 2006/0284095 A1 | * | 12/2006 | Muehllehner et al. .. 250/363.02 |

OTHER PUBLICATIONS

Moehrs et al, A detector head design for small-animal PET with silicon photomultipliers (SiPM), 2006, Phys. Med. Biol. 51 1113-1127.*

* cited by examiner

Primary Examiner—David P Porta
Assistant Examiner—Marcus H Taningco

(57) ABSTRACT

A brain imager includes a compact ring-like static PET imager mounted in a helmet-like structure. When attached to a patient's head, the helmet-like brain imager maintains the relative head-to-imager geometry fixed through the whole imaging procedure. The brain imaging helmet contains radiation sensors and minimal front-end electronics. A flexible mechanical suspension/harness system supports the weight of the helmet thereby allowing for patient to have limited movements of the head during imaging scans. The compact ring-like PET imager enables very high resolution imaging of neurological brain functions, cancer, and effects of trauma using a rather simple mobile scanner with limited space needs for use and storage.

15 Claims, 5 Drawing Sheets

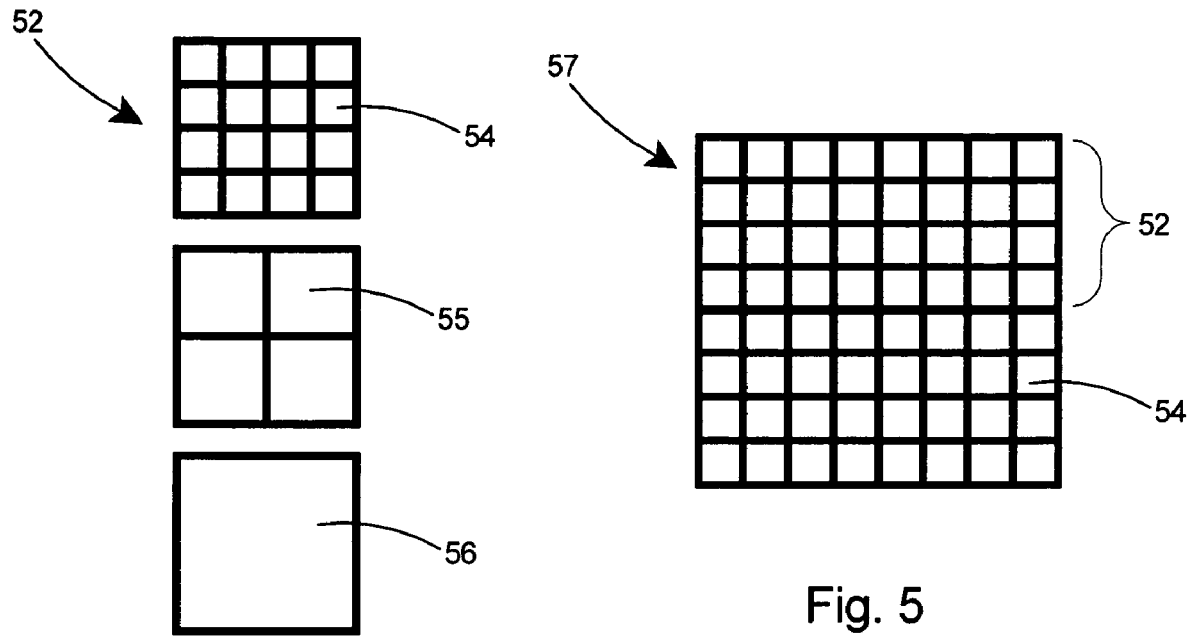
Fig. 4
Fig. 5
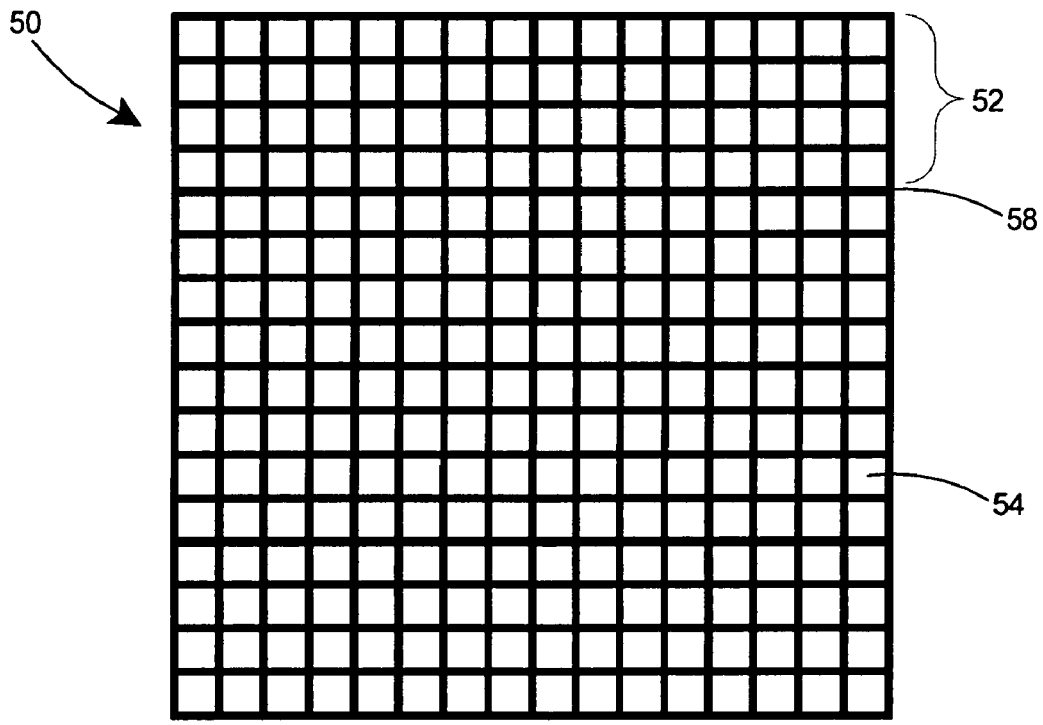
Fig. 6

COMPACT AND MOBILE HIGH RESOLUTION PET BRAIN IMAGER

The United States of America may have certain rights to this invention under Management and Operating contract No. DE-AC05-06OR23177 from the Department of Energy.

FIELD OF THE INVENTION

This invention relates to PET imaging and more particularly to a compact and mobile high resolution PET imaging system for imaging the neurological brain functions of a patient.

BACKGROUND OF THE INVENTION

Brain diseases, such as Alzheimer's and Parkinson's, are becoming more prevalent in the aging population because of increased life span. As US and European populations continue to age, Alzheimer's disease will increase with the US expected to have 16 million cases by 2050. An estimated 1.5 million people in the US have Parkinson's, which affects 1% of Americans over 60 and includes about 100,000 new cases each year.

Although many new PET radiopharmaceuticals for brain function imaging are under development, imaging modalities for the brain such as PET+CT and MRI+PET are insufficient due to poor PET resolution and poor CT/MRI/fMRI specificity. Current clinical PET scanners have a resolution of 4-5 mm, which is insufficient in many brain imaging situations. In addition, current clinical PET scanners are large, expensive, not optimized for brain imaging, and usually are available only in a package with CT. The existing standard PET imagers are bulky devices that are placed in dedicated imaging rooms and require patient to be brought to the imager. Some patients cannot be transported to the imaging room, which could be in a far away part of the medical complex, particularly in situations when they need to be hooked to life-saving and monitoring machines or when quick diagnostic and staging decision is important. In many other situations it would be an advantage to have the brain imaging scanner in an outpatient location, for example in a neurological department. In the current state of the art, brain imagers are bulky and heavy devices and are not capable of providing dynamic high resolution 2D or 3D images.

What is needed therefore, is a compact and mobile dedicated brain imager capable of producing dynamic high resolution 2D or 3D images. The compact and mobile imager should be capable of being easily attached to a patient's head to enable high resolution imaging of the patient's brain.

SUMMARY OF THE INVENTION

The present invention is a brain imager that includes a compact ring-like static PET imager mounted in a helmet-like structure. When attached to a patient's head, the helmet-like brain imager maintains the relative head-to-imager geometry fixed through the whole imaging procedure. The brain imaging helmet contains radiation sensors and minimal front-end electronics. A flexible mechanical suspension/harness system supports the weight of the helmet thereby allowing for patient to have limited movements of the head during imaging scans. The compact ring-like PET imager enables very high resolution imaging of neurological brain functions, cancer, and effects of trauma using a rather simple mobile scanner with limited space needs for use and storage.

OBJECTS AND ADVANTAGES

Several advantages are achieved with the compact high resolution brain imager of the present invention, including:

(1) The helmet-like brain imager maintains the relative head-to-imager geometry fixed through the whole imaging procedure thereby enhancing the accuracy of images.
(2) The brain imager provides high efficiency and high resolution in a compact application-specific device.
(3) The PET brain imager includes a high resolution of less than 2 mm.
(4) The higher spatial resolution of the proposed imager enables detection of smaller abnormalities and earlier detection and more accurate diagnosis of brain disease.
(5) As a result of being compact and mobile, the organ-specific imager can be moved to the patient, such as in the ER, ICU, hospital bed, or outpatient center, to provide in-situ imaging, especially when the patient cannot be moved to the PET imaging center
(6) The high-resolution and economical dedicated PET brain imager can have an important impact on early detection of brain disease and on therapy planning and monitoring.
(7) When used in combination with disease-specific biomarkers, the brain imager improves early diagnosis of the brain disease.
(8) The brain imager of the present invention can be adapted for use on other parts of the patient's body such as extremities, neck and thyroid, and the breast if reconfigured with a modified gantry.
(9) The brain imager includes a dedicated lightweight mobile gantry for stationary or optional translational/rotational scan.
(10) Real-time static tomographic imaging of an approximate 10 cm brain/head slice width and a field-of-view of less than 25 cm.
(11) Compact geometry allows close positioning while scanning the entire head.
(12) The brain imager provides 3D reconstructed resolution of less than 2.5 mm FWHM in the entire field-of-view (1.5-1.7 mm in center).
(13) Capable of fast continuous dynamic scans for high-quality complete angular sampling.

These and other objects and advantages of the present invention will be better understood by reading the following description along with reference to the drawings.

DESCRIPTION OF THE DRAWINGS

FIG. 4 depicts a basic initial 12.5 mm silicon PMT imaging module constructed of an array of sixteen 3 mm×3 mm readout pixels or pads arranged in a 4×4 array.

FIG. 5 depicts an array of 2×2 of the basic four-side buttable modules of FIG. 5 butted together to form an approximately one inch square photodetector.

FIG. 6 depicts the concept for a plug-in replacement module that can be implemented by arranging 16 (in array of 4×4) basic imaging modules.

Figure 1:
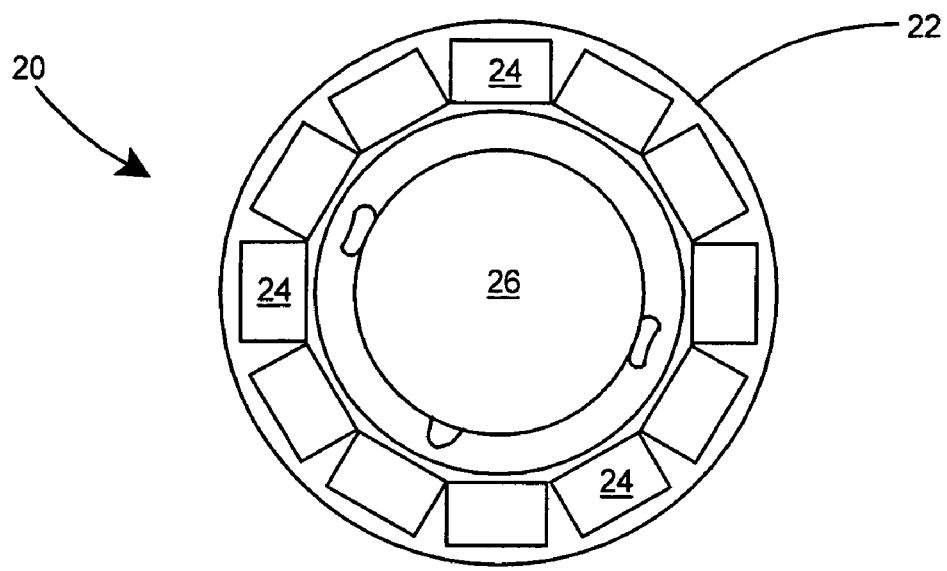
FIG. 1 is a conceptual view from above the patient's head of a brain imaging system according to the present invention including a ring of detector modules arranged around the patient's head.

INDEX TO REFERENCE NUMERALS IN DRAWINGS 20 brain imaging system, first embodiment
22 ring
24 photodetector module
26 patient
30 photodetector module, first embodiment
31 position sensitive photomultiplier tube (PSPMT)
32 readout electronics
33 scintillator array
34 window
35 reflective strip
36 dead region
37 outer shell or shield
40 photodetector module, second embodiment
43 Burle MCP PMT
44 optical spreader window
45 scintillation array
46 window
47 reflective strip
50 photodetector module, third and preferred embodiment
52 silicon PMT (SiPM) basic imaging module
54 basic silicon unit or pad
55 readout channel comprised of four pads
56 readout channel comprised of sixteen pads
57 one inch square silicon photodetector
58 dead region
60 brain imaging system, second embodiment
62 imager ring
64 photodetector module
66 scintillation array
68 photodetector
70 helmet imager
72 imaging ring
74 detector module
76 inner shell or liner
78 outer shell
79 hook
80 ring PET brain imager
81 mobile gantry
82 head
83 patient
84 treadmill
85 mechanical mount
86 suspension
87 counterweight

DETAILED DESCRIPTION OF THE INVENTION

With reference to FIG. 1 there is shown a compact and mobile brain imaging system 20 according to the present invention including a ring 22 with a set of photodetector modules 24 viewing the brain of a patient 26. A plurality of the photodetector modules 24 are formed into a ring 22 composed of 12-30 closely spaced and individually read imaging modules 24. The ring of imaging modules 24 provide enough surface coverage and angular views for high resolution 2D/3D PET image slice reconstruction of the brain.

A compact and mobile high resolution PET imager 20 according to the present invention would include a tomographic slice reconstruction of between 5 and 15 cm, and a 3D reconstruction resolution (over narrow slice involved) of between 1.5 and 2.0 mm. The compact ring imager 20 is preferably mounted in a suspended lightweight helmet with a 20 to 25 cm inner diameter opening for the head and neck. To limit detector volume and weight (including also less shielding), only minimal readout electronics are placed in the ring enclosure. Data acquisition (DAQ) electronics are located in a mobile cabinet (not shown), with small cross-section robust cable connection between the detector ring modules 24 and the DAQ module. The data acquisition and processing system is capable of recording data with at least 200 kHz trigger rate in a list mode, to enable prompt limited data analysis, and fast data replay and image reconstruction during the same scan session.

Several imaging technologies can be implemented in the brain imaging device of the present invention. The brain imager will preferably include a scintillator as a sensor/energy converter of 511 keV annihilation gamma rays, while various photodetectors serve as detectors of the scintillation light produced by the absorbed 511 keV gamma rays in the scintillator gamma sensor. The scintillator sensor part is preferably made of pixellated or plate crystal scintillator materials such as LSO, LYSO, GSO, BGO, LaBr3, NaI(Tl), CsI(Tl), CsI(Na), and other. The photodetector part is preferably a standard or multi-element photomultiplier, position sensitive, flat panel or microchannel plate based photomultiplier, avalanche photodiode arrays or large size avalanche photodiodes with resistive etc readout, and different variants of the silicon photomultiplier.

Figure 2:
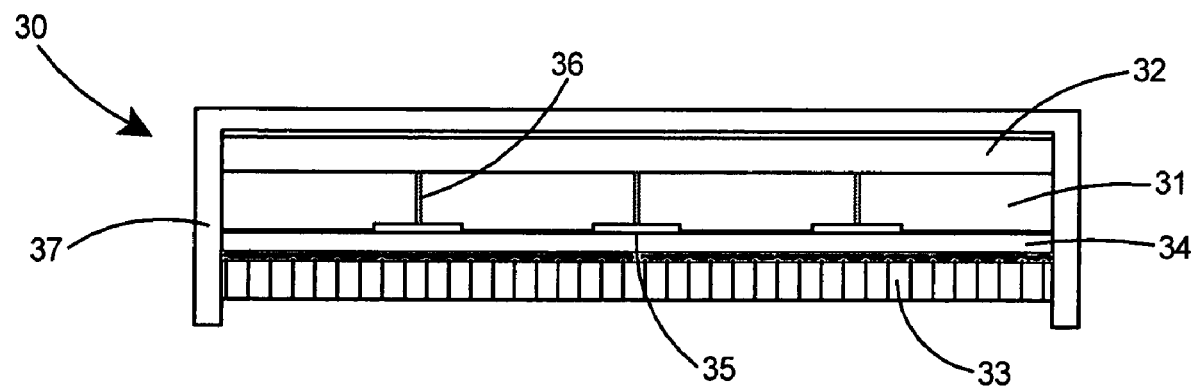
FIG. 2 is a sectional view of a PET imager detector module constructed using a modular approach according to the present invention.

Referring to FIG. 2 there is shown a first embodiment of a PET photodetector module 30 for constructing the compact brain imager of the present invention. The photodetector module 30 is based on compact, 1" or 2" in size, position sensitive photomultipliers (PSPMTs) 31 from Hamamatsu Corporation of Bridgewater, N.J. or Burle Industries of Lancaster, Pa. The photomultipliers 31 are coupled to an array 33 of 2×2×10 mm LYSO scintillator pixels. In the present invention, a modular approach is used in constructing the PET photodetector module 30. The detector module 30 includes an array of compact H8500 or H9500 flat panel PMTs 31 using high-rate resistive readout electronics 32. The position sensitive flat panel PMTs 31 are placed in a tight array and coupled to the scintillator array 33 through a window 34 and an optical light guide. The flat panel Hamamatsu H8500 or H9500 PMTs are each approximately 5 cm×5 cm in size, to obtain coverage of about 20 cm per detector module 30. Reflective strips 35 are placed in the dead regions 36 between the flat panel PMTs 31 to improve scintillation light collection from the approximately 2 cm wide dead regions 36 between the PMTs 31. An outer shell 37 is placed around the detector 30 for protection. The compact H8500 or H9500 flat panel PMTs, 1" or 2" in size, are available from Hamamatsu Corporation of Bridgewater, N.J.

Figure 3:
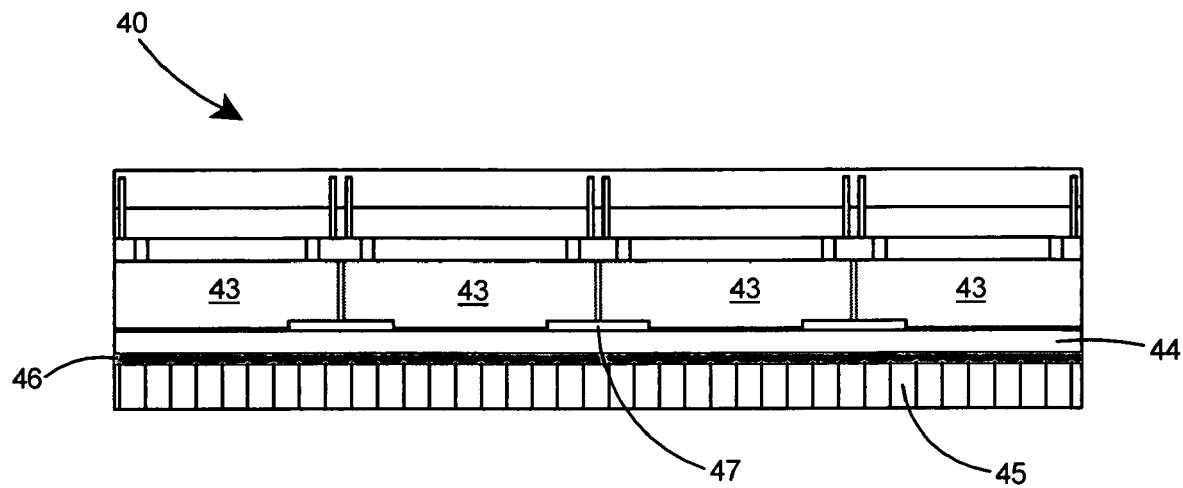
FIG. 3 is a sectional view of a PET imager detector module constructed using a modular approach according to the present invention.

Referring to FIG. 3 there is shown a second embodiment of a compact brain PET detector module 40 based on an array of 16 (4×4) Burle 85001-501 MCP (microchannel plates) PMTs 43 available from Burle Industries of Lancaster, Pa. The 85001-501 PMTs 43 are coupled through optical spreader window 44 to a scintillation array 45 encapsulated behind a window 46. Reflective strips 47 are placed in the dead regions between the MCP PMTs to improve scintillation light collection from ~2 cm wide dead regions between these MCP PMTs. The shielding is omitted in this figure.

Referring to FIGS. 4-6, a third and preferred embodiment of the PET detector head is produced using silicon photomultipliers (SiPMTs) in lieu of the position sensitive PMTs. The third embodiment of the photodetector module 50 is the preferred construction for the brain imager of the present invention as the SiPMTs provide a more compact and lighter weight imager. Typically SiPMT modules come in smaller size units of approximately 3 mm×3 mm to 5 mm×5 mm area and 1.5 mm in thickness. When combined with onboard electronics, the thickness of the SiPMT plus onboard electronics is less than 1 cm. Arrays of SiPMTs are needed to cover the desired active field of view. FIGS. 4-6 show an example of how to achieve a silicon PMT based photodetector 50 (FIG. 6) of approximately 5 cm×5 cm active field of view using nominal 12.5 mm silicon PMT basic imaging modules 52 (FIG. 4) each composed of sixteen 3 mm basic silicon PMT units 54. As shown in FIG. 4, the basic initial imaging module 52 can have an array of sixteen 3 mm×3 mm readout pixels or pads 54 arranged in a 4×4 array. The 3 mm pads or units 54 can be either read separately with four pads 54 connected to one readout channel 55 or coarsely 56 with all 16 pads 54 connected to one readout channel 56, as shown schematically at center and bottom of FIG. 4, respectively. As shown in FIG. 5, an array of 2×2 of these basic four-sides buttable modules (8×8=64 of 3 mm pads) forms an approximately 1" square photodetector 57 equivalent for example to a commercially available Hamamatsu R8520-C12 PSPMT. The basic imaging modules 52 will be four-side buttable with an estimated 1 mm dead space at the edges. As shown in FIG. 6, the photodetector modules are preferably arranged in major imaging modules 50 composed of 4×4 basic modules 52, with coverage and readout needs equivalent to the H8500 or H9500 flat panel PMT discussed hereinabove. The major imaging module 50 can be used as a plug-in replacement module for the H8500/H9500 flat panel PMT with an approximate 5 cm×5 cm active surface. The dead regions 58 between the basic modules will be about 1-2 mm wide, which will enable adequate scintillation signal sampling for uniform energy and spatial response. Silicon PMTs are available from several manufacturers including SensL USA of Mountain View, Calif. and Radiation Monitoring Devices, Inc. of Watertown, Mass.

Figure 7:
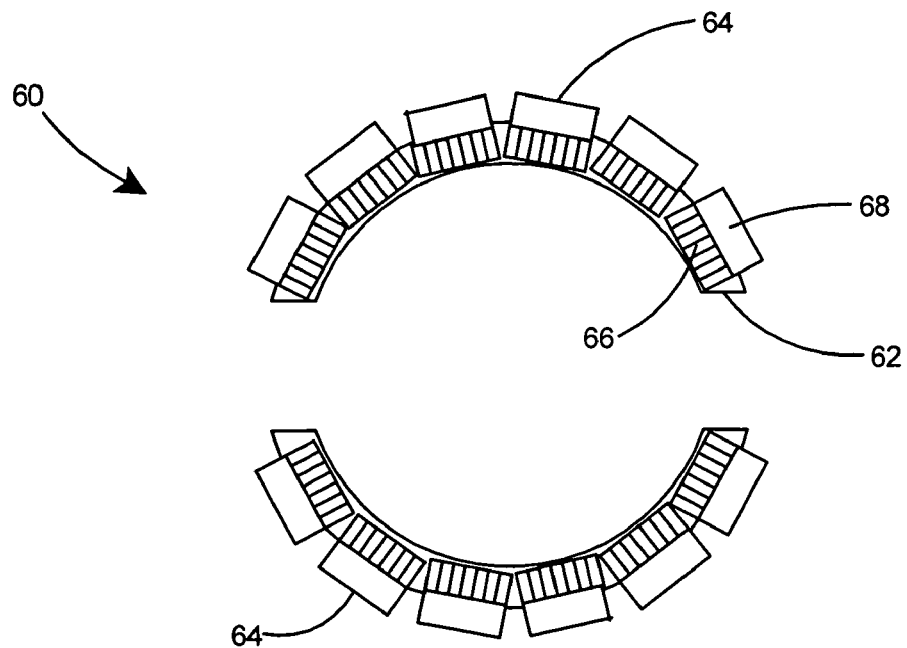
FIG. 7 is a conceptual view from above the patient's head of a single head/neck imager ring with 12 individual detector modules.

With reference to FIG. 7 there is shown a second embodiment of a brain imaging system 60 according to the present invention. The brain imager 60 includes a single head/neck imager ring 62 with 12 individual detector modules 64 as viewed from above the patient's head. To cover the active FOV of such a brain imager, the brain imager would be provided with a plurality of rings. In such a case, assuming an approximate 2"×2" size of each imager module, the imager would be provided with 1-3 rings, depending on the exact function of the imager and method of obtaining tomographic (3-dimensional) images in a static situation (no rotating parts). If information is desired on a specific region of the brain, a one-ring version of the imager can be positioned to image that region of the patient's brain or neck. c Each high rate capable detector module 64 is a separate entity with separate parallel readout and separate data acquisition channels to maximize overall rate capability. Each scintillation array 66 is coupled via proper optical light guide to a selected individual photodetector device 68.

Figure 8:
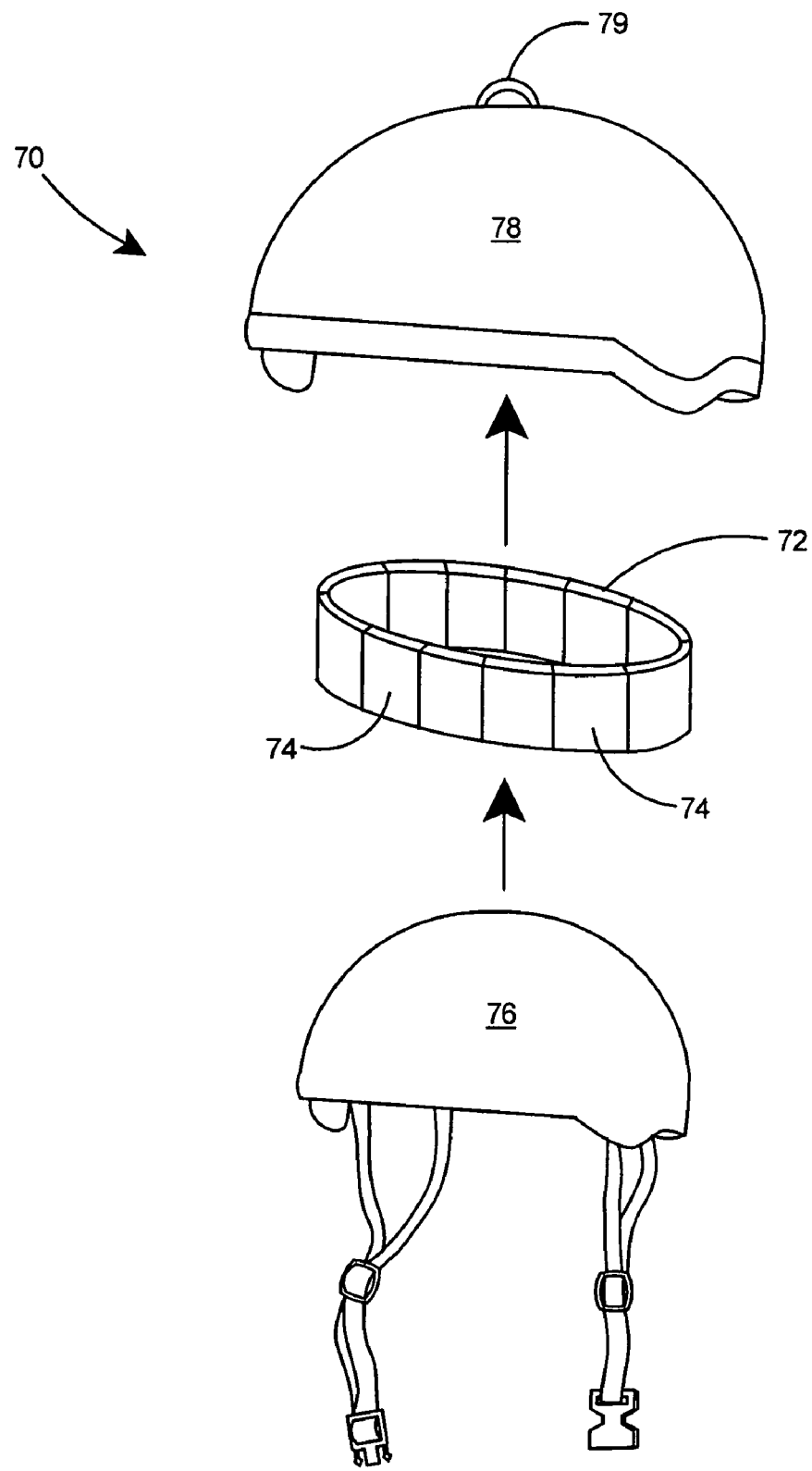
FIG. 8 is an exploded perspective view of a helmet brain imager according to the present invention.

With reference to FIG. 8, there is shown a helmet brain imager 70 according to the present invention. The helmet imager 70 includes a ring 72 of detector modules 74 attached to a rigid inner shell or liner 76. The inner liner 76 is mounted inside an outer cover or shell 78. The outer shell 78 includes an attached hook 79 for accommodating a harness or tether (not shown) for attaching to the outside suspension mechanism for supporting the weight of the imaging helmet 70. Electronics and cabling are omitted from the drawing.

Figure 9:
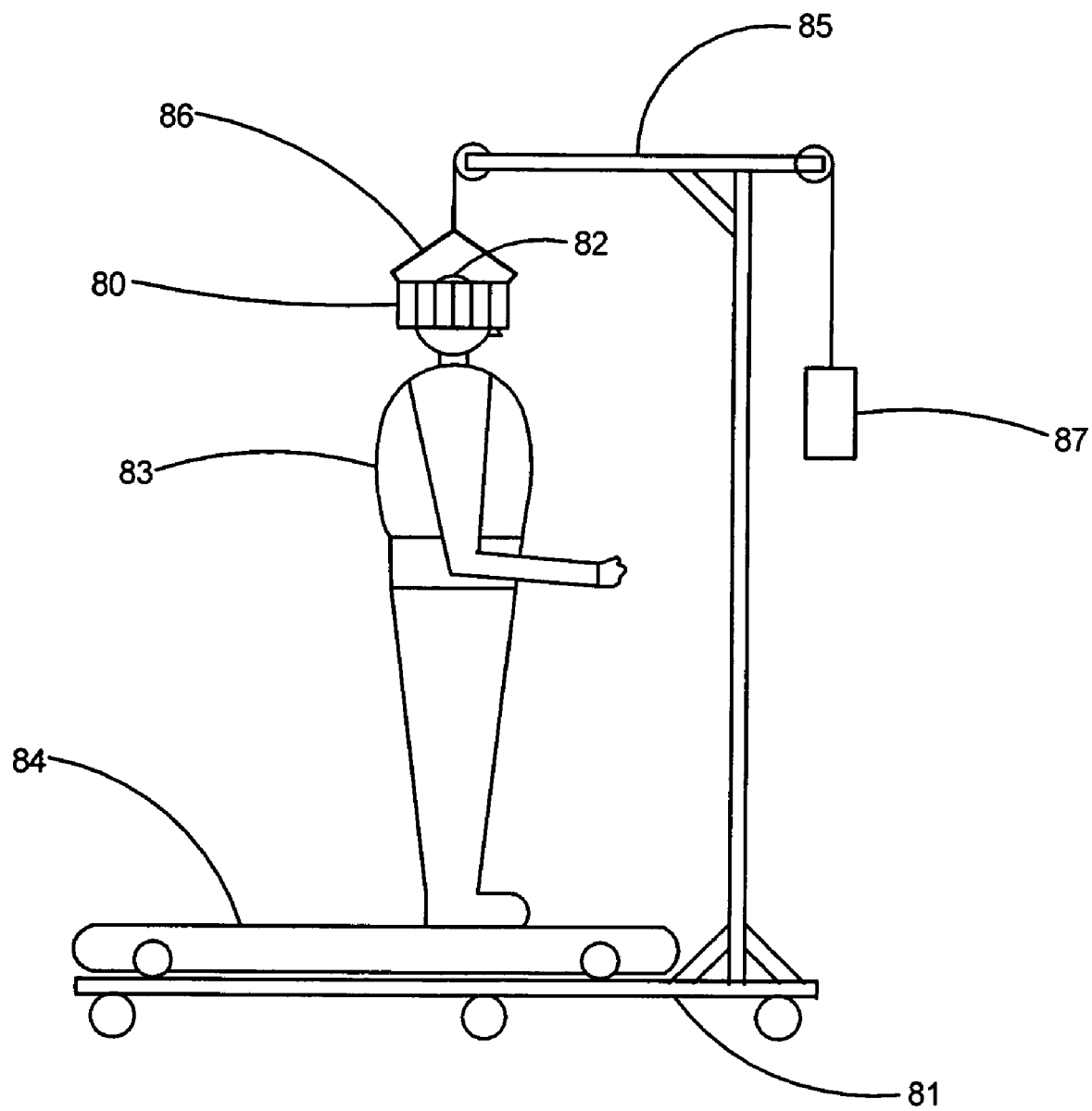
FIG. 9 is a side view of a ring PET brain imager 80 suspended from a mobile gantry and placed around the head of a patient that is exercising on a treadmill.

With reference to FIG. 9, there is shown an approximate 25 cm ring PET brain imager 80 suspended from a mobile gantry 81 around the head 82 of a patient 83 that is standing on a treadmill 84. FIG. 9 depicts a hypothetical imaging procedure to image a slice of the patient's brain to evaluate brain function and blood flow. The compact brain imager 80 of the present invention will be supported by a mechanical mount 85, suspension 86, and counterweight 87 to assure that the imager 80 is kept still relative to the patient's head 82 during the duration of the scan. The suspension 86 will support the weight of the imager 80 when placed on the patient's head 82 or neck. Although one support apparatus is shown in FIG. 9, other support schemes with the ring PET imager are possible, such as having the ring imager suspended from a rolling support on a spring or counterbalance to enable more flexible and comfortable placement of the imager. In any support arrangement, the helmet or ring brain imager ensures that small movements of the patient's body and head will be accommodated naturally with the imager helmet following the patient's movements.

At least four major categories of imager helmet support are possible, including: 1) attached to a fixture mounted in the ceiling of a room above a patient's chair, 2) attached to a fixture mounted above the patient's chair in the wall of the room on a rigid or articulate arm or bracket, 3) attached to a movable or rolling type support frame that can be moved along with the patient's chair, and 4) attached to an extension of an extended back support of the patient's chair itself, forming one compact mechanical unit.

Preferably, the weight of the helmet imager will be well-balanced by suspending it using a flexible support and will be attached to the patients head through straps or similar comfortable means. The critical aspect of the helmet imager of the present invention is to assure that the patient can move his or her body and head during the scan and the imager will follow all the head movements. At the required level of resolution of about 1-2 mm, any movements of the patient's head relative to the imager ring or rings would produce blurriness of the image and obstruct desired details of the image.

Monitoring of the position of patient's head or other organs is a serious consideration in cases of high resolution imaging when imaging modality requires a prolonged (longer than seconds) imaging procedure. Complicated means to monitor, such as optical sensors or magnetic sensors, and to correct in software for the organ movements, are implemented in many clinical imaging procedures. The helmet imager of the present invention and its secure attachment to the patient's head provides a significant advantage in that the complicated movement monitoring methods required in prior art imagers will be reduced to minimum.

The compact and mobile helmet imager of the present invention will provide high resolution and high-performance molecular imaging which, when used in combination with new biomarkers such as Pittsburgh Compound B (PiB) for detection of Alzheimer's, is expected to greatly improve early diagnosis of brain diseases. The detection and diagnoses of other diseases such as Parkinson's and Pick's disease will also be improved.

Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A helmet brain imager for imaging the entire brain of a compliant human patient comprising:
    a helmet including an inner shell mounted inside an outer shell;
    a plurality of closely spaced gamma detection modules mounted in a generally circular shape and secured to said inner shell of said helmet, said gamma detection modules for coincident detection of gamma annihilation photons;
    each of said gamma detection modules including a pixellated scintillator array and a single layer of basic imaging modules in a 4×4 array, said basic imaging modules including four-side buttable edges;
    each of said basic imaging modules including a 4×4 array of 3 mm basic silicon photomultiplier pads and onboard electronics having a thickness of less than 1 cm;
    said basic imaging modules including 1 mm dead spaces at said buttable edges;
    reflective strips in said dead spaces to improve scintillation light collection from said dead spaces;
    a strap for securing said helmet to the head of the patient in such a manner that the patient is able to move his or her body and head during an imaging scan and said helmet brain imager will follow all head movements by the patient;
    a suspension arrangement for supporting the weight of said helmet brain imager; and
    a data acquisition and processing system for accepting imaging data individually from each of said gamma detection modules for producing tomographic images of the brain.

2. The brain imaging system of claim 1 wherein said suspension arrangement includes a harness secured to a structure.

3. The brain imaging system of claim 1 wherein each of said gamma detection modules includes
    an imaging light guide extending from said scintillator array;
    a photo multiplier extending from said light guide; and
    a readout connected to said photo multiplier.

4. The brain imaging system of claim 3 wherein
    said gamma detection modules detect scintillation light produced by absorbed 511 keV gamma rays in the scintillator array; and
    said brain imaging system includes a spatial resolution of 2 mm or better.

5. The brain imaging system of claim 1 including
    a multiple ring imager; and
    said multiple ring imager including three or more of said imaging rings arranged on top of one another whereby said multiple ring imager maximizes the imaged target volume and the system sensitivity and enables imaging of the entire brain in one scanning position.

6. The brain imaging system of claim 1 including real-time static tomographic imaging of an approximate 10 cm brain slice width and a field-of-view of less than 25 cm.

7. The brain imaging system of claim 1 including 3D reconstructed resolution of less than 2.5 mm FWHM in the entire field-of-view.

8. The brain imaging system of claim 1 including
    a tomographic slice reconstruction of between 5 and 15 cm; and
    a 3D reconstruction resolution of between 1.5 and 2.0 mm over the narrow slice involved.

9. The brain imaging system of claim 1 wherein said data acquisition and processing system includes
    a data recording rate of at least 200 kHz trigger rate in a list mode to enable prompt limited data analysis; and
    fast data replay and image reconstruction during the same scan session.

10. The brain imaging system of claim 1 wherein said helmet brain imager includes between 12 and 30 of said gamma detection modules.

11. The brain imaging system of claim 1 wherein said gamma detection modules include
    a scintillator as a sensor and energy converter of 511 keV annihilation gamma rays; and
    a photodetector to detect the scintillation light produced by the absorbed gamma rays in the scintillator.

12. The brain imaging system of claim 11 wherein said scintillator includes
    pixellated or plate crystal scintillator materials; and
    said scintillator materials are selected from the group including LSO, LYSO, GSO, BGO, LaBr3, NaI(Tl), CsI(Tl), and CsI(Na).

13. The brain imaging system of claim 11 wherein said photodetector is selected from the group including standard photomultiplier, multi-element photomultiplier, position sensitive photomultiplier, flat panel photomultiplier, microchannel plate based photomultiplier, avalanche photodiode array, large size avalanche photodiode with resistive readout, and silicon photomultiplier.

14. The brain imaging system of claim 1 wherein said gamma detection modules include
    silicon photomultipliers with an area of between 3 mm×3 mm to 5 mm×5 mm area and a thickness of 1.5 mm.

15. The brain imaging system of claim 1 wherein said gamma detection modules include
    a photodetector with a 5 cm×5 cm active field of view;
    said gamma detection modules detect scintillation light produced by absorbed 511 keV gamma rays; and
    said brain imaging system includes a spatial resolution of 2 mm or better.

* * * * *